(12) United States Patent
Dupuis

(10) Patent No.: US 6,592,854 B1
(45) Date of Patent: Jul. 15, 2003

(54) COSMETIC COMPOSITION CONTAINING AN ANIONIC OR NONIONIC POLYMER AND A CARBOXYLIC SILICON

(75) Inventor: Christine Dupuis, Paris (FR)

(73) Assignee: L'Oréal S. A., Paris (FR)

(*) Notice: Subject to any disclaimer, the term of this patent is extended or adjusted under 35 U.S.C. 154(b) by 0 days.

(21) Appl. No.: 09/297,977

(22) PCT Filed: Oct. 27, 1997

(86) PCT No.: PCT/FR97/01922
§ 371 (c)(1), (2), (4) Date: Jul. 14, 1999

(87) PCT Pub. No.: WO98/20833
PCT Pub. Date: May 22, 1998

(30) Foreign Application Priority Data

Nov. 12, 1996 (FR) .............................. 96 13759

(51) Int. Cl.⁷ .............................................. A61K 7/06
(52) U.S. Cl. ................ 424/70.1; 424/401; 424/70.4; 424/70.11; 424/70.12; 424/70.16; 424/70.22
(58) Field of Search ................ 424/401, 70.1, 424/70.11, 70.12, 70.16, 70.22

(56) References Cited

U.S. PATENT DOCUMENTS

| | | | |
|---|---|---|---|
| 2,047,398 A | 7/1936 | Voss et al. | |
| 2,102,113 A | 12/1937 | Djordjevitch | |
| 2,723,248 A | 11/1955 | Wright | |
| 4,128,631 A | 12/1978 | Lundmark et al. | |
| 4,693,935 A | 9/1987 | Mazurek | |
| 4,728,571 A | 3/1988 | Clemens et al. | |
| 4,844,888 A | * 7/1989 | Zawadzki | 429/69 |
| 4,972,937 A | 11/1990 | Aarts | |
| 5,660,820 A | * 8/1997 | Mondet et al. | 424/70.16 |
| 5,690,924 A | * 11/1997 | Keil et al. | 429/78.03 |

FOREIGN PATENT DOCUMENTS

| | | |
|---|---|---|
| DE | 2 330 956 | 1/1974 |
| EP | 0 219 830 | 4/1987 |
| EP | 0 412 704 | 2/1991 |
| EP | 0 412 707 | 2/1991 |
| EP | 0 582 152 | 2/1994 |
| FR | 1 222 944 | 6/1960 |
| FR | 1 564 110 | 4/1969 |
| FR | 1 580 545 | 9/1969 |
| FR | 2 198 719 | 4/1974 |
| FR | 2 265 782 | 10/1975 |
| FR | 2 265 871 | 10/1975 |
| FR | 2 350 384 | 12/1977 |
| FR | 2 357 241 | 2/1978 |
| FR | 2 439 798 | 5/1980 |
| GB | 0 839 805 | 6/1960 |
| WO | WO 92/21316 | 12/1992 |
| WO | WO 92/23009 | 11/1993 |
| WO | WO 93/23446 | 11/1993 |
| WO | WO 95/00108 | 1/1995 |
| WO | WO 95/00578 | 1/1995 |
| WO | 95/23579 | * 8/1995 |
| WO | WO 95/23579 | 9/1995 |

OTHER PUBLICATIONS

Amihud Kramer, "Revised Tables for Determining Significance of Differences", Journal of the Institute of Food Technologists, Food Technology, vol. 17, No. 11, Nov. 1963, pp. 124–125.
English language Derwent Abstract of DE 2 330 956, Jan. 1974
English language Derwent Abstract of FR 1 564 110, Jan. 1969.
English language Derwent Abstract of FR 1 580 545, Jan. 1969.
English language Derwent Abstract of FR 2 198 719, Apr. 1974.
English language Derwent Abstract of FR 2 265 781, Nov. 1975.
English Language Derwent Abstract of FR 2 265 782, Nov. 1975.
English language Derwent Abstract of FR 2 350 384, Oct. 1978.
English language Derwent Abstract of FR 2 357 241, Feb. 1978.
English Language Derwent Abstract of FR 2 439 798, Feb. 1980.

* cited by examiner

Primary Examiner—Thurman K. Page
Assistant Examiner—Lakshmi Channavajjala
(74) Attorney, Agent, or Firm—Finnegan, Henderson, Farabow, Garrett & Dunner, LLP

(57) ABSTRACT

The invention concerns a cosmetic composition for treating keratinous fibers, in particular hair, containing at least an anionic or non-ionic polymer and at least one silicon comprising at least a carboxylic acid function, as well as the method for treating keratinous fibers using this composition.

33 Claims, No Drawings

COSMETIC COMPOSITION CONTAINING AN ANIONIC OR NONIONIC POLYMER AND A CARBOXYLIC SILICON

The present invention relates to a cosmetic composition for treating keratin fibres, in particular the hair, comprising at least one anionic or nonionic polymer and at least one silicone comprising at least one carboxylic acid function, as well as to the process for treating keratin fibres using this composition.

Compositions for holding or shaping the hair containing styling polymers (fixing polymers) in their formulation generally have the drawback of making the hair difficult to disentangle, restyle or blow-wave, in particular during brushing. Hair treated with these fixing polymers is generally coarse and has an unnatural feel.

The combination of silicone derivatives with fixing polymers is known in cosmetic compositions for holding and/or fixing the hairstyle. It has been found that these silicone derivatives can improve the disentangling, softness and sheen properties of hair treated with these compositions. However, silicone derivatives are not favourable to the styling properties of compositions containing fixing polymers and the disentangling and softness properties are still not satisfactory.

The aim of the present invention is thus to propose compositions for fixing and/or shaping the hairstyle, these compositions needing to have good properties of fixing and/or hold over time and needing to provide excellent cosmetic properties such as softness, disentangling and feel.

Hair compositions containing a cationic polymer and a polydimethylsiloxane containing carboxylic functionality are known from document EP-A-0,219,830. However, the addition of the polydimethylsiloxane does not improve the softness properties of hair treated with a cationic polymer.

The Applicant has now discovered, surprisingly, that by using compositions containing an anionic or nonionic polymer in combination with at least one silicone comprising at least one carboxylic acid function in a cosmetically acceptable medium, excellent cosmetic properties such as softness, disentangling and feel are obtained while at the same time obtaining excellent styling and/or fixing properties.

A subject of the present invention is thus a cosmetic composition, in particular for keratin fibres, comprising, in a cosmetically acceptable medium, at least one anionic or nonionic polymer and at least one silicone comprising at least one carboxylic acid function.

In the context of the present application, the expression "cosmetic compositions for holding the hairstyle" means any composition whose function is to temporarily fix the shape of the hairstyle, such as, for example, styling lacquers and sprays and styling gels and mousses. The expression "fixing power of the composition" denotes the ability of this composition to give the hair cohesion such that the initial shaping of the hairstyle is maintained. The term "fixing polymer" means any polymer whose function is to fix the shape of the hairstyle.

According to the present invention, the term "keratin fibres" is intended to refer to the hair, the eyelashes and the eyebrows, and more particularly the hair.

According to the present invention, the term "carboxylic acid group" is intended to refer to the free acid form, the form neutralized with a base, and mixtures thereof. According to the invention, the carboxylic acid group does not result from the polymerization of one or more anionic monomers containing ethylenic unsaturation.

In all of the text hereinabove and hereinbelow, in accordance with what is generally accepted, the term "silicone" is intended to denote any organosilicon polymer or oligomer with a linear or cyclic, branched or crosslinked structure, of variable molecular weight, obtained by polymerization and/or polycondensation of suitably functionalized silanes, and consisting essentially of a repetition of main units in which the silicon atoms are linked together by oxygen atoms (siloxane bonding ≡Si-O-Si≡), optionally substituted hydrocarbon-based radicals being linked directly via a carbon atom to the said silicon atoms. The most common hydrocarbon-based radicals are alkyl radicals, especially $C_1$–$C_{10}$ alkyl radicals and in particular methyl, fluoroalkyl radicals, and aryl radicals and in particular phenyl.

The silicone comprising at least one carboxylic acid group can be an organopolysiloxane comprising at least one unit:

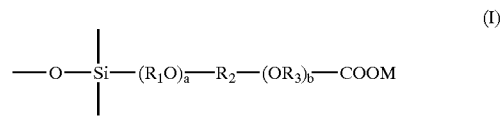

(I)

in which $R_1$ and $R_3$ independently denote a linear or branched alkylene radical containing from 2 to 20 carbon atoms and $R_2$ denotes a linear or branched alkylene radical containing from 1 to 50 carbon atoms which can comprise a hydroxyl group, a represents 0 or 1, b is a number ranging from 0 to 200 and M denotes hydrogen, an alkali metal or alkaline-earth metal, $NH_4$ or a quaternary ammonium group such as a mono-, di-, tri- or tetra($C_1$–$C_4$ alkylammonium) group, $R_1$ and $R_3$ can denote, for example, ethylene, propylene or butylene.

It is possible to use, for example, the organopolysiloxanes containing carboxylic groups, of formula (II):

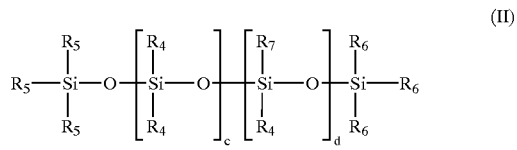

(II)

in which the radicals $R_4$ are identical to or different from each other and are chosen from a linear or branched $C_1$–$C_{22}$ alkyl radical, a $C_1$–$C_{22}$ alkoxy radical and a phenyl radical, the radicals $R_5$, $R_6$ and $R_7$ are identical to or different from each other and are chosen from a linear or branched $C_1$–$C_{22}$ alkyl radical, a $C_1$–$C_{22}$ alkoxy radical, a phenyl radical and a radical —$(R_1O)_a$—$R_2$—$(OR_3)_b$—COOM, at least one of the radicals $R_5$, $R_6$ and $R_7$ being a radical —$(R_1O)_a$—$R_2$—$(OR_3)_b$—COOM, the radicals $R_1$, $R_2$, $R_3$, a, b and M having the same meaning as above, c and d are integers from 0 to 1000, the sum c+d preferably ranging from 2 to 1000.

Among the silicones of formula (II), the preferred ones are the compounds of formula (III) below:

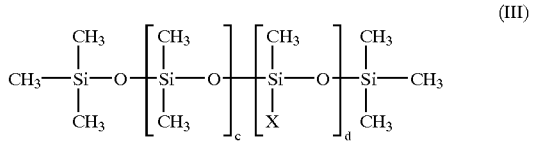
(III)

in which X is a radical —(R$_1$O)$_a$—R$_2$—(OR$_3$)$_b$—COOM, the radicals R$_1$, R2, R$_3$, a, b, d and M having the same meaning as above.

Even more particularly, the compounds of formula (III) in which a and b are equal to 0 and R$_2$ is a linear or branched C$_2$–C$_{12}$ alkylene group such as (CH$_2$)$_9$, (CH$_2$)$_{10}$ or —CH(CH$_3$)— are preferred.

The silicones comprising at least one carboxylic acid group are described in particular in patent applications WO 95/23579 and EP-A-0,219,830.

Compounds corresponding to formula (III) above are sold, for example, under the name Huile M 642 by the company Wacker, under the names SLM 23 000/1 and SLM 23 000/2 by the company Wacker, under the name 176–12057 by the company General Electric, under the name FZ 3703 by the company OSI and under the name BY 16 880 by the company Toray Silicone.

According to the invention, any anionic or nonionic fixing polymer known per se can be used.

These fixing polymers can be used in dissolved form or in the form of dispersions of solid polymer particles.

The anionic fixing polymers generally used are polymers containing groups derived from carboxylic, sulphonic or phosphoric acids and have a weight-average molecular weight of approximately between 500 and 5,000,000.

1) The carboxylic groups are provided by unsaturated mono- or dicarboxylic acid monomers such as those corresponding to the formula:

(IV)

in which n is an integer from 0 to 10, A$_1$ denotes a methylene group, optionally connected to the carbon atom of the unsaturated group, or to the neighbouring methylene group when n is greater than 1, via a hetero atom such as oxygen or sulphur, R$_{10}$ denotes a hydrogen atom or a phenyl or benzyl group, R$_8$ denotes a hydrogen atom or a lower alkyl or carboxyl group, R$_9$ denotes a hydrogen atom, a lower alkyl group or a —CH$_2$—COOH, phenyl or benzyl group.

In the abovementioned formula, a lower alkyl radical preferably denotes a group having 1 to 4 carbon atoms and in particular methyl and ethyl.

The anionic fixing polymers containing carboxylic groups which are preferred according to the invention are:

A) Homo- or copolymers of acrylic or methacrylic acid or salts thereof and in particular the products sold under the names Versicol E or K by the company Allied Colloid and Ultrahold by the company BASF. The copolymers of acrylic acid and of acrylamide sold in the form of their sodium salt under the names Reten 421, 423 or 425 by the company Hercules, the sodium salts of polyhydroxycarboxylic acids.

B) Copolymers of acrylic or methacrylic acids with a monoethylenic monomer such as ethylene, styrene, vinyl esters, acrylic acid esters or methacrylic acid esters. These copolymers can be grafted onto a polyalkylene glycol such as polyethylene glycol and optionally crosslinked. Such polymers are described in particular in French patent 1,222,944 and German patent application 2,330,956. Mention may be made in particular of copolymers containing in their chain an optionally N-alkylated and/or hydroxyalkylated acrylamide unit as described in particular in Luxembourg patent applications 75370 and 75371 or sold under the name Quadramer by the company American Cyanamid. Mention may also be made of copolymers of acrylic acid and of C$_1$–C$_4$ alkyl methacrylate and terpolymers of vinylpyrrolidone, of (meth)acrylic acid and of (meth)acrylate of C$_1$–C$_{20}$ alkyl, for example of lauryl (such as that sold by the company ISP under the name Acrylidone LM), of tert-butyl (Luviflex VBM 70 sold by BASF) or of methyl (Stepanhold Extra sold by Stepan) and methacrylic acid/ethyl acrylate/tert-butyl acrylate/terpolymers such as the product sold under the name Luvimer 100 P by the company BASF.

C) Copolymers derived from crotonic acid such as those containing vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Such polymers are described, inter alia, in French patents 1,222,944, 1,580,545, 2,265,782, 2,265,781, 1,564,110 and 2,439,798. Commercial products falling into this class are the resins 28-29-30, 26-13-14 and 28-13-10 sold by the company National Starch.

D) Copolymers derived from C$_4$–C$_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, acrylic acid and its esters, the anhydride functions of these copolymers optionally being monoesterified or monoamidated. Such polymers are described in particular in U.S. Pat. Nos. 2,047,398, 2,723,248 and 2,102,113 and GB patent 839,805, and in particular those sold under the names Gantrez AN or ES and Avantage CP by the company ISP.

copolymers comprising (i) one or more maleic, citraconic or itaconic anhydrides and (ii) one or more monomers chosen from allylic or methallylic esters optionally containing one or more acrylamide, methacrylamide or α-olefin group, acrylic or methacrylic esters, acrylic or methacrylic acids or vinylpyrrolidone in their chain, the anhydride functions of these copolymers optionally being monoesterified or monoamidated. These polymers are described, for example, in French patents 2,350,384 and 2,357,241 by the Applicant.

E) Polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be chosen in particular from:

polyvinylsulphonic acid salts having a weight-average molecular weight of approximately between 1000 and 100,000, as well as the copolymers with an unsaturated comonomer such as acrylic or methacrylic acids and their esters, as well as acrylamide or its derivatives, vinyl ethers and vinylpyrrolidone;

polystyrenesulphonic acid salts, the sodium salts having a weight-average molecular weight of about 500,000 and about 100,000, which are sold respectively under the names Flexan 500 and Flexan 130 by National Starch. These compounds are described in patent FR 2,198, 719;

polyacrylamidesulphonic acid salts, those mentioned in U.S. Pat. No. 4,128,631 and more particularly polyacrylamidoethylpropanesulphonic acid sold under the name Cosmedia Polymer HSP 1180 by Henkel.

According to the invention the anionic fixing polymers are preferably chosen from acrylic acid copolymers such as the acrylic acid/ethyl acrylate/N-tert-butylacrylamide terpolymers sold under the name Ultrahold Strong by the company BASF, copolymers derived from crotonic acid such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids or anhydrides with vinyl esters, vinyl ethers, vinyl halides, phenylvinyl derivatives or acrylic acid and its esters, such as the methyl vinyl ether/maleic anhydride monoesterified copolymers sold, for example, under the name Gantrez by the company ISP, the copolymers of methacrylic acid and of methyl methacrylate sold under the name Eudragit L by the company Rohm Pharma, the copolymers of methacrylic acid/methyl methacrylate/C1–C4 alkyl acrylate/acrylic acid or C1–C4 hydroxyalkyl methacrylate sold in the form of dispersions under the name Amerhold DR 25 by the company Amerchol or under the name Acudyne 255 by the company Rohm & Haas, the copolymers of methacrylic acid and of ethyl acrylate sold under the name Luvimer MAEX or MAE by the company BASF and vinyl acetate/crotonic acid copolymers and vinyl acetate/crotonic acid copolymers grafted with polyethylene glycol under the name Aristoflex A by the company BASF.

The anionic fixing polymers most particularly preferred are chosen from the monoesterified methyl vinyl ether/ maleic anhydride copolymers sold under the name Gantrez ES 425 by the company ISP, the acrylic acid/ethyl acrylate/ n-tert-butylacrylamide terpolymers sold under the name Ultrahold Strong by the company BASF, the copolymers of methacrylic acid and of methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer MAEX or MAE by the company BASF and the vinylpyrrolidone/acrylic acid/lauryl methacrylate terpolymers sold under the name Acrylidone LM by the company ISP.

The nonionic fixing polymers which can be used according to the present invention are chosen, for example, from:

vinyllactam homopolymers such as polyvinylpyrrolidone and polyvinylcaprolactam;

vinyllactam copolymers such as copolymers of vinylpyrrolidone and of vinyl acetate and vinylpyrrolidone/ vinyl acetate/vinylpropionate copolymers;

polyalkyloxazolines such as the polyethyloxazolines sold by the company Dow Chemical under the names PEOX 50,000, PEOX 200,000 and PEOX 500,000;

vinyl acetate homopolymers such as the product sold under the name Appretan EM by the company Hoechst or the product sold under the name Rhodopas A 012 by the company Rhône-Poulenc;

copolymers of vinyl acetate and of acrylic ester, such as the product sold under the name Rhodopas AD 310 by Rhône-Poulenc;

copolymers of vinyl acetate and of ethylene, such as the product sold under the name Appretan TV by the company Hoechst;

copolymers of vinyl acetate and of maleic ester, for example dibutyl maleate, such as the product sold under the name Appretan MB Extra by the company Hoechst;

copolymers of polyethylene and of maleic anhydride;

alkyl acrylate homopolymers and alkyl methacrylate homopolymers, such as the product sold under the name Micropearl RQ 750 by the company Matsumoto or the product sold under the name Luhydran A 848 S by the company BASF;

acrylic ester copolymers such as, for example, copolymers of alkyl acrylates and of alkyl methacrylates, such as the products sold by the company Rohm & Haas under the names Primal AC-261 K and Eudragit NE 30 D, by the company BASF under the names Acronal 601, Luhydran LR 8833 or 8845, and by the company Hoechst under the names Appretan N 9213 or N9212;

copolymers of acrylonitrile and of a nonionic monomer chosen, for example, from butadiene and alkyl (meth) acrylates, such as the products sold under the names Nipol LX 531 B by the company Nippon Zeon or those sold under the name CJ 0601 B by the company Rohm & Haas;

polyurethanes, such as the products sold under the names Acrysol RM 1020 or Acrysol RM 2020 by the company Rohm & Haas, the products Uraflex XP 401 UZ and Uraflex XP 402 UZ by the company DSM Resins;

copolymers of alkyl acrylate and of urethane, such as the product 8538-33 by the company National Starch;

polyamides, such as the product Estapor LO 11 by the company Rhône-Poulenc;

chemically modified or unmodified nonionic guar gums.

The unmodified nonionic guar gums are, for example, the products sold under the name Vidogum GH 175 by the company Unipectine and under the name Jaguar C by the company Meyhall.

The modified nonionic guar gums which can be used according to the invention are preferably modified with $C_1$–$C_6$ hydroxyalkyl groups. Mention may be made, by way of example, of hydroxymethyl, hydroxyethyl, hydroxypropyl and hydroxybutyl groups.

These guar gums are well known in the state of the art and can be prepared, for example, by reacting the corresponding alkylene oxides such as, for example, propylene oxides with guar gum so as to obtain a guar gum modified with hydroxypropyl groups.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

The alkyl radicals in the nonionic polymers contain from 1 to 6 carbon atoms, except where otherwise mentioned.

According to the invention, it is also possible to use anionic or nonionic fixing polymers of grafted silicone type comprising a polysiloxane portion and a portion consisting of a non-organosilicone chain, one of the two portions constituting the main chain of the polymer, the other being grafted onto the said main chain. These polymers are described, for example, in patent applications EP-A-0,412,704, EP-A-0,412,707, EP-A-0,640,105 and WO 95/00578, EP-A-0,582,152 and WO 93/23009 and U.S. Pat. Nos. 4,693,935, 4,728,571 and 4,972,937.

Such polymers are, for example, the copolymers which can be obtained by radical polymerization from the monomer mixture consisting of:
 a) 50 to 90% by weight of tert-butyl acrylate;
 b) 0 to 40% by weight of acrylic acid;
 c) 5 to 40% by weight of silicone macromer of formula:

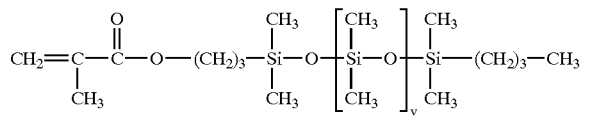

with v being an integer ranging from 5 to 700; the percentages by weight being calculated relative to the total weight of the monomers.

Other examples of grafted silicone polymers are, in particular, polydimethylsiloxanes (PDMSs) onto which are grafted, via a linker chain of thiopropylene type, mixed polymer units of the poly(meth)acrylic acid type and of the poly(alkyl methacrylate) type and polydimethylsiloxanes (PDMSs) onto which are grafted, via a linker chain of thiopropylene type, polymer units of the poly(isobutyl (meth)acrylate) type.

According to the present invention, the fixing polymers are preferably anionic polymers.

The anionic fixing polymers can be partially or totally neutralized, if necessary. The neutralizing agents are, for example, sodium hydroxide, potassium hydroxide, 2-amino-2-methyl-1-propanol, monoethanol-amine, triethanolamine or triisopropanolamine, and inorganic or organic acids such as hydrochloric acid or citric acid.

The fixing polymer(s) is (are) present, for example, in concentrations of between 0.05% and 20% by weight, and preferably in concentrations of between 0.1% and 10% by weight, relative to the total weight of the composition.

The silicone(s) containing carboxylic groups can be present in concentrations of between 0.01% and 10% by weight, and preferably in concentrations of between 0.05% and 5% by weight and even more particularly from 0.1 to 2% by weight, relative to the total weight of the composition.

The cosmetically acceptable medium generally comprises water, one or more cosmetically acceptable solvents or a mixture of water and cosmetically acceptable solvent(s).

The cosmetically acceptable medium preferably comprises one or more cosmetically acceptable solvents.

The concentration of cosmetically acceptable solvent is generally greater than 20% by weight relative to the total weight of the composition.

The water concentration is generally less than 80% by weight relative to the total weight of the composition.

The cosmetically acceptable solvents are, for example, monoalcohols, polyalcohols, glycol ethers or fatty acid esters, which can be used alone or as a mixture. These solvents are preferably $C_1$–$C_6$ alcohols.

Among these alcohols, mention may be made of ethanol, isopropanol, polyalcohols such as diethylene glycol, glycol ethers including the monoalkyl ethers of ethylene glycol, of diethylene glycol, of propylene glycol or of dipropylene glycol. Ethanol is particularly preferred.

The composition of the invention can also contain at least one additive chosen from thickeners, fatty acid esters, fatty acid esters of glycerol, volatile or non-volatile silicones which are soluble or insoluble in the composition, surfactants, fragrances, preserving agents, sunscreens, proteins, vitamins, ceramides, pseudoceramides, polymers, plant, animal, mineral or synthetic oils and any other additive conventionally used in cosmetic compositions for keratin fibres.

More particularly, the composition also comprises at least one cationic polymer.

These additives are present in the composition according to the invention in proportions which can range from 0 to 20% by weight relative to the total weight of the composition. The precise amount of each additive depends on its nature and is readily determined by a person skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of thickened or unthickened lotion, cream or milk.

The compositions according to the invention can be used as rinse-out products and preferably as leave-in products, in particular for treating the hair, holding the hairstyle or shaping keratin fibres such as the hair.

A subject of the invention is also the use of a composition as defined above as, or for the manufacture of, a care, styling or fixing composition for the hair.

These compositions are, more particularly, styling products such as fixing compositions (lacquers) and styling compositions. The lotions can be packaged in various forms, in particular in vaporizers, pump-dispenser bottles or in aerosol containers in order to apply the composition in vaporized form or in the form of a mousse. Such packaging forms are indicated, for example, when it is desired to obtain a spray, a lacquer or a mousse for fixing or treating the hair.

When the composition according to the invention is packaged in aerosol form in order to obtain an aerosol mousse or lacquer, it comprises at least one propellant which can be chosen from volatile hydrocarbons such as n-butane, propane, isobutane and pentane, a chlorinated and/or fluorinated hydrocarbon and mixtures thereof. Carbon dioxide, nitrous oxide, dimethyl ether, nitrogen or compressed air, and mixtures thereof, can also be used as propellant.

According to the invention, the propellant concentration is generally between 5 and 90% by weight relative to the total weight of the composition, and preferably between 10 and 70% by weight. The pressurized compositions in aerosol mousse form preferably comprise from 5 to 30% by weight of propellant relative to the total weight of the composition.

A subject of the invention is also a process for the cosmetic treatment of keratin fibres such as the hair, which consists in applying a composition as defined above to these fibres.

The compositions according to the invention are prepared according to methods which are well known in the state of the art. In particular, the ingredients are mixed together and are then packaged in a suitable container depending on the use envisaged.

The invention will now be illustrated more fully with the aid of the examples which follow, which cannot be considered as limiting it to the embodiments described. (In the text hereinbelow, AM means Active Material).

EXAMPLE 1

Three lacquers of the composition below were prepared:

| FORMULATION TESTED | A (invention) | B (comparative) | C (comparative) |
|---|---|---|---|
| Carboxylic silicone*[1] | 1 g | — | — |
| Oxyalkylenated silicone*[3] | — | 1 g | — |
| Anionic polymer*[2] | 4 g | 4 g | 4 g |
| Ethanol qs | 100 g | 100 g | 100 g |

*[1]Polydimethylsiloxane containing undecylenic groups (Huile M642 sold by the company Wacker)
*[2]Acrylic acid/ethyl acrylate/N-tert-butylacrylamide terpolymer sold under the name Ultrahold Strong by the company BASF
*[3]Polydimethylsiloxane containing oxyalkylene groups (Dow Corning 190 Fluid sold by the company Dow Corning)

Pressurization Scheme:

Above composition: 65 g

Dimethyl ether 35 g 65 g of the above composition are introduced into an aerosol container, a valve is crimped on and the dimethyl ether is then introduced.

Each of these compositions was applied to locks of washed and dried hair.

The disentangling and the softness of the hair treated with these lacquers was then compared by means of a sensory evaluation test.

The object of the test used is to classify, by means of a panel consisting of 12 experts, a series of 3 locks as an increasing or decreasing function of the disentangling efficacy (ease of passing a comb through) and the softness. The 3 locks are simultaneously presented to the expert. He or she is asked to classify them from the easiest to disentangle to the most difficult and from the softest to the least soft. The statistical analysis of the results is carried out using the tables by A. Kramer (Food Technology 17-(12), 124–125 1963).

The results are given in Tables I and II below.

TABLE 1

Disentangling

| EXPERTS LACQUERS | 1 | 2 | 3 | 4 | 5 | 6 | 7 | 8 | 9 | 10 | 11 | 12 | SUM OF THE ROWS |
|---|---|---|---|---|---|---|---|---|---|---|---|---|---|
| A | 1 | 1 | 1 | 1 | 1 | 1 | 1 | 1 | 1 | 1 | 1 | 1 | 12 |
| B | 2 | 2 | 2 | 2 | 2 | 2 | 2 | 2 | 2 | 2 | 2 | 2 | 24 |
| C | 3 | 3 | 3 | 3 | 3 | 3 | 3 | 3 | 3 | 3 | 3 | 3 | 36 |

TABLE II

Softness

| EXPERTS LACQUERS | 1 | 2 | 3 | 4 | 5 | 6 | 7 | 8 | 9 | 10 | 11 | 12 | SUM OF THE ROWS |
|---|---|---|---|---|---|---|---|---|---|---|---|---|---|
| A | 1 | 1 | 1 | 1 | 2 | 1 | 1 | 1 | 1 | 2 | 1 | 1 | 14 |
| B | 2 | 2 | 2 | 2 | 1 | 2 | 2 | 2 | 2 | 1 | 2 | 2 | 22 |
| C | 3 | 3 | 3 | 3 | 3 | 3 | 3 | 3 | 3 | 3 | 3 | 3 | 36 |

According to the Kramer tables, if the sum of the rows for a composition is outside the range 18–30 (3 samples—12 experts), this composition is significantly different from the other compositions.

Composition A according to the invention therefore has superior disentangling and softness properties to those of composition B and C.

EXAMPLE 2 (COMPARATIVE)

Three lacquers not in accordance with the invention, of the composition below, were prepared:

| FORMULATION TESTED | A (comparative) | B (comparative) | C (comparative) |
|---|---|---|---|
| Carboxylic silicone*[1] | 1 g | — | — |
| Oxyalkylenated silicone*[3] | — | 1 g | — |
| Cationic polymer*[2] | 5.7 g AM | 5.7 g AM | 5.7 g AM |
| Ethanol qs | 100 g | 100 g | 100 g |

*[1]Polydimethylsiloxane containing undecylenic groups (Wacker Huile M642)
*[2]Vinylcaprolactam/vinylpyrrolidone/dimethylaminoethyl methacrylate terpolymer sold under the name Gaffix VC 713 by the company ISP
*[3]Polydimethylsiloxane containing oxyalkylene groups (Dow Corning 190 Fluid sold by the company Dow Corning)

Pressurization Scheme:

Above composition: 65 g

Dimethyl ether 35 g 65 g of the above composition are introduced into an aerosol container, a valve is crimped on and the dimethyl ether is then introduced.

Each of these compositions was applied to locks of washed and dried hair.

The softness of the hair treated with these lacquers was then compared by means of a sensory evaluation test.

A panel of 10 experts was thus asked to classify the locks treated with each composition according to the criterion of softness.

Composition A containing the silicone containing a carboxylic group and a cationic polymer has inferior softness properties to those of composition B containing an oxyalkylenated silicone, and the same level of softness properties as those of the composition containing only the cationic polymer.

The carboxylic silicone thus does not make it possible to improve the softness of hair treated with a cationic polymer.

EXAMPLE 3

Two lacquers of the composition below were prepared:

| FORMULATION TESTED | A (invention) | B (comparative) |
|---|---|---|
| Carboxylic silicone*[1] | 1 g | — |
| Oxyalkylenated silicone*[3] | — | 1 g |
| Nonionic polymer*[2] | 4 g AM | 4 g AM |
| Ethanol qs | 100 g | 100 g |

*[1]Polydimethylsiloxane containing undecylenic groups (Huile M642 sold by the company Wacker)
*[2]Polyvinylcaprolactam
*[3]- Polydimethylsiloxane containing oxyalkylenated groups (Dow Corning 190 Fluid sold by the company Dow Corning)

Pressurization Scheme:

Above composition: 65 g

Dimethyl ether 35 g 65 g of the above composition are introduced into an aerosol container, a valve is crimped on and the dimethyl ether is then introduced.

Each of these compositions was applied to two half-heads of washed and dried hair.

A panel of 10 experts was then asked to evaluate the disentangling and softness and the fixing power of the locks treated with each composition.

Composition A (invention) has superior fixing power and softness properties than those of composition B.

EXAMPLE 4

A fixing spray composition packaged in an aerosol container, of the composition below, was prepared:

acrylic acid/ethyl acrylate/N-tert-butylacrylamide terpolymer sold under the name Ultrahold Strong by the company BASF 4 g 2-amino-2-methyl-1-propanol qs 100% neutralization of the terpolymer polydimethylsiloxane containing undecylenic groups, sold under the name Huile M642 by the company Wacker 1 g ethanol qs 100 g Pressurization Scheme:

Above composition: 65 g

Dimethyl ether 35 g 65 g of the above composition are introduced into an aerosol container, a valve is crimped on and the dimethyl ether is then introduced.

Hair treated with the composition according to the invention has good feel, softness and disentangling properties.

EXAMPLE 5

A fixing spray composition packaged in an aerosol container, of the composition below, was prepared:

acrylic acid/ethyl acrylate/N-tert-butylacrylamide terpolymer sold under the name Ultrahold Strong by the company BASF 2.3 g 2-amino-2-methyl-1-propanol qs 100% neutralization of the terpolymer vinylcaprolactam/vinylpyrrolidone/dimethylaminoethyl methacrylate terpolymer sold under the name Gaffix VC 713 by the company ISP 3.8 g AM polydimethylsiloxane containing undecylenic groups, sold under the name Huile M642 by the company Wacker 0.8 g ethanol qs 100 g Pressurization Scheme:

Above composition: 65 g

Dimethyl ether 35 g 65 g of the above composition are introduced into an aerosol container, a valve is crimped on and the dimethyl ether is then introduced.

EXAMPLE 6

A fixing spray composition packaged in a pump-dispenser bottle, of the composition below, was prepared:

vinyl acetate/vinyl p-tert-butyl-benzoate/crotonic acid terpolymer (fixing polymer) 5 g 2-amino-2-methyl-1-propanol (qs 100l neutralization of the fixing polymer)

polydimethylsiloxane containing undecylenic groups, sold under the name Huile M642 by the company Wacker 1 g ethanol qs 100 g

EXAMPLE 7

A fixing spray composition packaged in a pump-dispenser bottle, of the composition below, was prepared:

polyvinylcaprolactam 6 g AM polydimethylsiloxane containing undecylenic groups, sold under the name Huile M642 by the company Wacker 1.2 g water 37.8 g ethanol qs 100 g

EXAMPLE 8

A styling mousse of the composition below was prepared:

acrylic acid/ethyl acrylate/N-tert-butylacrylamide terpolymer sold under the name Ultrahold Strong by the company BASF (fixing polymer) 2 g 2-amino-2-methyl-1-propanol (qs 100% neutralization of the fixing polymer)

polydimethylsiloxane containing undecylenic groups, sold under the name Huile M642 by the company Wacker 1 g polyvinylcaprolactam 1 gAM mixture of cetylstearyl alcohol and cetyl-stearyl alcohol oxyethylenated with 5 mol of ethylene oxide, sold under the name Polawax A 31 by the company Croda 0.5 g ethanol 25 g water qs 100 g Aerosol Packaging:

90 g of the above composition are packaged in an aerosol container in the presence of 10 g of a ternary mixture of n-butane, isobutane and propane (23/55/22), sold under the name "Aerogaz 3.2 N" by the company Elf Aquitaine.

The composition is applied to hair, washed andtowel-dried. It leads to good holding of hairstyle and good disentangling and softness properties.

What is claimed is:

1. A cosmetic composition, comprising, in a cosmetically acceptable medium:

at least one fixing polymer chosen from anionic and nonionic fixing polymers; and at least one silicone comprising at least one carboxylic acid function, wherein said at least one silicone is chosen from organopolysiloxanes comprising at least one unit (I):

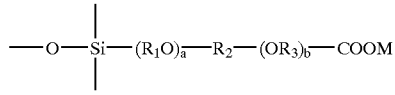
(I)

in which:
R$_1$ and R$_3$ are independently chosen from linear and branched C$_2$–C$_{20}$ alkylene radicals;
R$_2$ is chosen from linear and branched C$_1$ to C$_{50}$ alkylene radicals, said radicals optionally comprising a hydroxyl group;
a represents 0 or 1;
b is a number ranging from 0 to 200; and
M is chosen from hydrogen, alkali metals, alkaline-earth metals, NH$_4$, and quaternary ammonium groups.

2. The cosmetic composition of claim 1, wherein said at least one fixing polymer is present in said composition in an amount ranging from 0.05 to 20% by weight of said composition.

3. The cosmetic composition of claim 2, wherein said at least one fixing polymer is present in said composition in an amount ranging from 0.1 to 10% by weight.

4. The cosmetic composition of claim 1, wherein said at least one silicone is present in said composition in an amount ranging from 0.01 to 10% by weight of said composition.

5. The cosmetic composition of claim 4, wherein said at least one silicone is present in said composition in an amount ranging from 0.05 to 5% by weight.

6. The cosmetic composition of claim 5, wherein said at least one silicone is present in said composition in an amount ranging from 0.1 to 2% by weight.

7. The cosmetic composition of claim 1, wherein M is chosen from quaternary ammonium groups, and further wherein said quaternary ammonium groups are chosen from mono-, di, tri-, and tetra-(C$_1$ to C$_4$ alkylammonium) groups.

8. The cosmetic composition of claim 1, wherein R$_1$ and R$_3$ are chosen from ethylene, propylene and butylene.

9. The cosmetic composition of claim 1, wherein said organopolysiloxanes are chosen from compounds of formula (II):

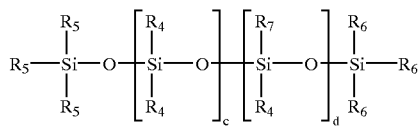
(II)

in which:
R$_4$ is chosen from linear and branched C$_1$–C$_{22}$ alkyl radicals, C$_1$–C$_{22}$ alkoxy radicals and phenyl radicals, and wherein each R$_4$ is independently selected;
R$_5$, R$_6$ and R$_7$ are identical or different from each other and are chosen from linear and branched C$_1$–C$_{22}$ alkyl radicals, C$_1$–C$_{22}$ alkoxy radicals, a phenyl radical, and —(R$_1$O)$_a$—R$_2$—(OR$_3$)$_b$—COOM radicals, wherein at least one of said R$_5$, R$_6$ and R$_7$ is a radical —(R$_1$O)$_a$—R$_2$—(OR$_3$)$_b$—COOM, R$_1$, R$_2$, R$_3$, a, b, and M being defined as in claim 1, and
c and d are each an integer ranging from 0 to 1000.

10. The cosmetic composition of claim 9, wherein said organopolysiloxanes are compounds of formula (III):

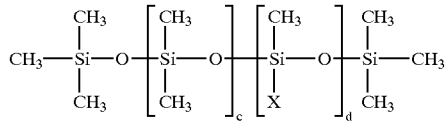

in which X is a radical —(R$_1$O)$_a$—R$_2$—(OR$_3$)$_b$—COOM, and R$_1$, R$_2$, R$_3$, a, b, c, d, and M are defined as in claim 9.

11. The cosmetic composition of claim 10, wherein a and b are both 0 and R$_2$ is chosen from linear and branched C$_2$–C$_{12}$ alkylene groups.

12. The cosmetic composition of claim 11, wherein R$_2$ is chosen from (CH$_2$)$_9$, (CH$_2$)$_{10}$, and —CH(CH$_3$)—.

13. The cosmetic composition of claim 9, wherein the sum of c+d ranges from 2 to 1000.

14. The cosmetic composition of claim 1, wherein said at least one fixing polymer is chosen from anionic polymers comprising at least one carboxylic acid group, anionic polymers comprising at least one sulphonic acid group, and anionic polymers comprising at least one phosphoric acid group, and salts thereof, and wherein said anionic polymer has a weight-average molecular weight ranging from 500 to 5,000,000.

15. The cosmetic composition of claim 14, wherein in said anionic polymers comprising at least one carboxylic acid group, said at least one carboxylic acid group is chosen from mono- and dicarboxylic acid monomers having the formula (IV):

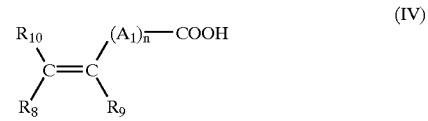
(IV)

in which:
n is a number ranging from 0 to 10;
A$_1$ is a methylene group, optionally connected to the carbon atom of the unsaturated group, or to the neighboring methylene group when n is greater than 1, via a hetero atom;
R$_8$ is chosen from a hydrogen atom, lower alkyl groups and carboxyl groups;
R$_9$ is chosen from a hydrogen atom, lower alkyl groups, —CH$_2$—COOH, a phenyl group, and a benzyl group; and
R$_{10}$ is chosen from a hydrogen atom, a phenyl group and a benzyl group.

16. The cosmetic composition of claim 15, wherein the hetero atom is chosen from oxygen and sulphur and the lower alkyl groups of R$_8$, R$_9$, or both, are chosen from C$_1$–C$_4$.

17. The cosmetic composition of claim 14, wherein said anionic polymers containing at least one carboxylic acid group are chosen from:
homo- and copolymers of acrylic and methacrylic acid;
copolymers formed from crotonic acid;
copolymers formed from: (I) at least one monomer chosen from maleic, fumaric and itaconic acids and anhydrides and (ii) at least one monomer chosen from vinyl esters, vinyl ethers, vinyl halides, phenylvinyl derivatives, acrylic acid and acrylic acid esters, the anhydride functions of said copolymers being optionally monoesterified or monoamidated;
copolymers formed from: (I) at least one monomer chosen from maleic, citraconic and itaconic acids and anhydrides and (ii) at least one monomer chosen from allylic esters and methallylic esters, said allylic and methallylic esters optionally containing at least one group chosen from acrylamide, methacrylamide and aolephin groups, acrylic esters, methacrylic esters, acrylic acids, methacrylic acids, and vinylpyrrolidone, the anhydride functions of said copolymers being optionally monoesterified or monoamidated;

copolymers formed from methacrylic acid and methylmethacrylate;

copolymers formed from methacrylic acid and ethyl acrylate;

and salts thereof.

18. The cosmetic composition of claim 17, wherein said anionic polymers. are acrylic acid copolymers chosen from acrylic acid/ethyl acrylate/N-tert-butylacrylamide terpolymers and salts thereof.

19. The cosmetic composition of claim 17, wherein said anionic copolymers are crotonic acid copolymers chosen from vinyl acetate/vinyl tert-butylbenzoate/crotonic acid terpolymers, crotonic acid/vinyl acetate/vinyl neododecanoate terpolymers; vinyl acetate/crotonic acid copolymers, vinyl acetate/crotonic copolymers grafted with polyethylene glycol, vinyl acetate/crotonic acid/polyethylene glycol terpolymers and salts thereof.

20. The cosmetic composition of claim 17, wherein said anionic copolymers are copolymers formed from monomers chosen from maleic, fumaric and itaconic acids and anhydrides.

21. The cosmetic composition of claim 20, wherein said anionic copolymers are chosen from methyl vinyl ether/maleic anhydride monoesterified copolymers and salts thereof.

22. The cosmetic composition of claim 17, wherein said anionic polymer is chosen from monoesterified methyl vinyl ether/maleic anhydride copolymers; acrylic acid/ethyl acrylate/n-tert-butylacrylamide terpolymers; copolymers of methacrylic acid and methyl methacrylate; vinyl acetate/vinyl tert-butylbenzoate/crotonic acid terpolymers; crotonic acid/vinyl acetate/vinyl neododecanoate terpolymers; copolymers of methacrylic acid and ethyl acrylate; vinylpyrrolidone/acrylic acid/lauryl methacrylate terpolymers; and salts thereof.

23. The cosmetic composition of claim 14, wherein said anionic polymers containing at least one sulphonic acid group are selected from polymers containing at least one monomeric residue formed from vinylsulphonic, styrenesulphonic, naphtholenesulphonic, and acrylamidoalkylsulphonic monomers, and salts thereof.

24. The cosmetic composition of claim 1, wherein said at least one fixing polymer is chosen from nonionic polymers.

25. The cosmetic composition of claim 24, wherein said nonionic polymers are chosen from vinyllactam homopolymers; vinylactam copolymers; polyalkyloxazolines; vinyl acetate homopolymers; copolymers of vinyl acetate and of acrylic ester; copolymers of vinyl acetate and of ethylene; copolymers of vinyl acetate and of maleic ester; copolymers of polyethylene and of maleic anhydride; alkyl acrylate homopolymers; alkyl methacrylate homopolymers; acrylic ester copolymers; copolymers of acrylonitrile and of a nonionic monomer; copolymers of alkyl acrylate and urethane; polyamides; and salts thereof.

26. The cosmetic composition of claim 24, wherein said vinyllactam homopolymers are chosen from polyvinyl pyrrolidone and polyvinylcaprolactam.

27. The cosmetic composition of claim 24, wherein said vinyllactam copolymers are chosen from vinylpyrrolidone/vinyl acetate/vinyl proprionate copolymers, copolymers of vinylpyrrolidone and of vinyl acetate; and salts thereof.

28. The cosmetic composition of claim 1, wherein said cosmetically acceptable medium comprises water, at least one cosmetically acceptable solvent, or a mixture of water and at least one cosmetically acceptable solvent.

29. A process for the treatment of keratin fibers comprising applying to said keratin fibers in a cosmetically acceptable medium an effective amount of cosmetic composition comprising, at least one fixing polymer chosen from anionic and nonionic fixing polymers; and at least one silicone comprising at least one carboxylic acid function, wherein said at least one silicone is chosen from organopolysiloxanes comprising at least one unit (I):

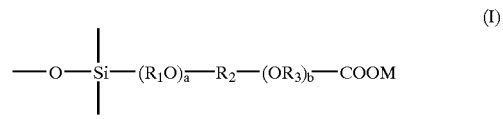

in which:

$R_1$ and $R_3$ are independently chosen from linear and branched $C_2$–$C_{20}$ alkylene radicals;

$R_2$ is chosen from linear and branched $C_1$ to $C_{50}$ alkylene radicals, said radicals optionally comprising a hydroxyl group;

a represents 0 or 1;

b is a number ranging from 0 to 200; and

M is chosen from hydrogen, alkali metals, alkaline-earth metals, $NH_4$, and quaternary ammonium groups.

30. The cosmetic composition of claim 29, wherein said keratin fibers are hair.

31. The process of claim 29, wherein said treatment includes caring for, styling of, or fixing keratin fibers.

32. A cosmetic composition, comprising, in a cosmetically acceptable medium:

at least one silicone comprising at least one carboxylic acid function; and at least one fixing polymer chosen from an anionic polymer comprising at least one sulphonic acid group, wherein said anionic polymer comprising at least one sulphonic acid group is chosen from polymers containing at least one monomeric residue formed from vinylsulphonic, styrenesulphonic, naphtholenesulphonic, and acrylamidoalkylsulphonic monomers, and salts thereof, and wherein said anionic polymer has a weight-average molecular weight ranging from 500 to 5,000,000.

33. A process for the treatment of keratin fibers comprising applying to said keratin fibers in a cosmetically acceptable medium an effective amount of cosmetic composition comprising, at least one silicone comprising at least one carboxylic acid function; and at least one fixing polymer that is an anionic polymer comprising at least one sulphonic acid group, wherein said anionic polymer containing at least one sulphonic acid group is chosen from polymers containing at least one monomeric residue formed from vinylsulphonic, styrenesulphonic, naphtholenesulphonic, and acrylamidoalkylsulphonic monomers, and salts thereof, and wherein said anionic polymer has a weight-average molecular weight ranging from 500 to 5,000,000.

* * * * *